United States Patent [19]

Kanegae et al.

[11] Patent Number: 5,268,279
[45] Date of Patent: Dec. 7, 1993

[54] METHOD FOR PRODUCING POLYGLUTAMIC ACID OR A SALT THEREOF

[75] Inventors: Yukihiro Kanegae, Kobe; Yoshio Sugiyama, Takasago; Isamu Nakatsui, Kobe, all of Japan

[73] Assignee: Takeda Chemical Industries, Ltd., Osaka, Japan

[21] Appl. No.: 556,372

[22] Filed: Jul. 23, 1990

[30] Foreign Application Priority Data

Jul. 26, 1989 [JP] Japan ................................ 1-193653

[51] Int. Cl.$^5$ ......................... C12P 21/04; C12R 1/10; C12R 1/12
[52] U.S. Cl. .................... 435/71.2; 435/71.1; 435/836; 435/839
[58] Field of Search ............... 435/71.1, 71.2, 836, 435/839

[56] References Cited

PUBLICATIONS

Chemical Abstracts, vol. 63, 1965, p. 3339, "IV. Chemical constituents of mucilage in natto. 2."
Chemical Abstracts, vol. 68, 1968, p. 58521r, "Polyglutamic acid fermentation."
Sawao Murao, "Polyglutamic acid fermentation" Kobunshi, 16(188), pp. 1204–1212 (1967).
Hisao Fujii, "Formation of mucilage by *Bacillus natto*. N. Chemical constituents of mucilage in natto. 2." Nippon Nogei Kagaku Kaishi (Jnl. of Agric. Chem. Soc. of Japan) 37(8), pp. 474–477 (1963).
C. Gomez Leonard et al., "Effects of Some Metallic Ions on Glutamy Polypeptide Synthesis by *Bacillus Subtilis*" Journal of Bacteriology, vol. 76, pp. 499–503 (1958).
R. M. Ward et al., "Polyglutamic Acid Production by *Bacillus subtilis* NRRL B–612 Growth on Wheat Gluten", Biotechnology and Bioengineering, vol. V, pp. 41–48 (1963).

*Primary Examiner*—Herbert J. Lilling
*Attorney, Agent, or Firm*—Wegner, Cantor, Mueller & Player

[57] ABSTRACT

In a fermentive production of polyglutamic acid and a salt thereof, the accumulation of polyglutamic acid can be markedly increased in a very simple manner by adding an alkaline earth metal ion to the medium in a concentration of not less than 0.05 mole per liter.

3 Claims, No Drawings

METHOD FOR PRODUCING POLYGLUTAMIC ACID OR A SALT THEREOF

FIELD OF THE INVENTION

This invention relates to a method for producing polyglutamic acid and a salt thereof which are expected to be useful as functional materials in food, cosmetic, medicinal, textile and other industries.

BACKGROUND OF THE INVENTION

A method well known in the art for producing polyglutamic acid consists in organic synthesis. From the industrial viewpoint, however, this method cannot be said to be an advantageous method, since it comprises polymerizing glutamic acid through a number of complicated reactions.

On the other hand, a number of reports have been presented on the fermentative production of polyglutamic acid using microorganisms since the publication of Bovarnick's work in 1942. Thus, for example, a method of producing polyglutamic acid is known which comprises cultivating a bacterial strain of the genus Bacillus, as described in Journal of Bacteriology, 76, 499 (1958), Journal of the Agricultural Chemical Society of Japan, 37, 474 (1963), or Kobunshi (High Polymers, Japan), 16, 1204 (1967).

As mentioned above, it is known that certain microorganisms can produce polyglutamic acid, and it is believed that, from the industrial viewpoint, the fermentative production of polyglutamic acid is more advantageous as compared with the chemical synthesis. It is still desired, however, that the yield should be further increased so that this substance can be supplied at reduced prices for wider application thereof in various fields.

OBJECT OF THE INVENTION

An object of the invention is to provide a method for producing a polyglutamic acid and a salt thereof advantageously on a commercial scale.

SUMMARY OF THE INVENTION

The present invention relates to a method for producing a polyglutamic acid and a salt thereof which comprises cultivating a microorganism capable of producing a polyglutamic acid in a medium containing an alkaline earth metal ion in a concentration of not less than 0.05 mole per liter.

DETAILED DESCRIPTION OF THE INVENTION

The microorganism to be used in the practice of the invention may be any polyglutamic acid producer, without any limitation on its taxonomical position. Polyglutamic acid producing strains belonging to the genus Bacillus are preferred, however. As such microorganisms of the genus Bacillus, there may be mentioned polyglutamic acid producers of the species *Bacillus subtilis* and *Bacillus licheniformis*, for instance. More particularly, *Bacillus subtilis* S-2 (IFO 14898, deposited as FERM BP-2528, at the Fermentation Research Institute Agency of Industrial Science and Technology, Japan) and *Bacillus licheniformis* IFO 12107, among others, may be mentioned as typical producer strains. The strain *Bacillus subtilis* S-2 is a mutant derived from *Bacillus subtilis* IFO 14187 (Japanese Patent Laid Open Publication No. 42895/1984) by NTG treatment and exhibits remarkable stringiness. A typical method of its derivation comprises smearing a medium (pH 7.0) containing 50 g of glucose, 15 g of monosodium glutamate, 2.7 g of $KH_2PO_4$, 4.2 g of $Na_2HPO_4 \cdot 12H_2O$, 0.5 g of NaCl, 0.5 g of $MgSO_4 \cdot 7H_2O$, 2 mg of $MnSO_4 \cdot nH_2O$, 100 µg of biotin and 15 g of agar per liter with the parent strain treated with N-methyl-N',-nitro-N-nitrosoguanidine, examining the resultant colonies for the stringiness and selecting a strain showing said ability at a highest level.

The IFO 12107 strain is a known strain deposited with the Institute for Fermentation Osaka (IFO) and can be found on the List of Cultures, 8th edition (1988) published by said institute.

Generally, Bacillus strains are readily changeable in their properties and can readily undergo spontaneous mutation as well as artificial mutation induced, for example, by X ray irradiation, ultraviolet irradiation, radiation induction or treatment with an artificial mutagen. Any mutant can be used in the practice of the invention provided that it is capable of producing polyglutamic acid.

As the alkaline earth metal ion to be added to the medium in accordance with the invention, there may be mentioned the calcium ion, magnesium ion and barium ion. While the substance to serve as a source of such ion is not critical, the ion is preferably added to the medium in the form of a carbonate, hydroxide, phosphate or nitrate, for instance, and more preferably in the form of a carbonate or hydroxide. The alkaline earth metal ion source may be added directly to the medium and, in cases where glutamic acid is used as a component of the medium, for example as a substrate, it is most preferable that glutamic acid and an alkaline earth metal salt be admixed together in advance for neutralization, followed by addition to the medium.

The alkaline earth metal ion source may be added to the seed culture medium, or to the medium for the fermentation proper, or a part of said source may be added to the seed culture medium and the remainder to the fermentation medium. In general, it is advantageous that most of the source substance be added in 5 to 6 hours after start of fermentation. Some alkaline earth metal ion sources may serve also as pH adjusting agents in the medium for fermentation. The medium pH is selected generally in the range of 6 to 7.5, preferably in the range of about 6.5 to about 7.0.

The alkaline earth metal ion concentration should be not less than 0.05 mole per liter, usually within the range of 0.05 to 0.3 mole per liter, preferably within the range 0.1 to 0.2 mole per liter. In cases where glutamic acid is used as a substrate, it is preferable that concentration be at least a half of equimolar to glutamic acid.

Other medium components may be those medium components used in the prior art fermentative production of polyglutamic acid. Thus, for example, glucose, fructose, sucrose, crude sugar, molasses (e.g. beet molasses, sugarcane molasses) and saccharification products derived from various kinds of starch (e.g. tapioca, sago palm, sweet potato, potato, corn) may be used as carbon sources. Usable as nitrogen sources are organic nitrogen sources, such as peptone, soybean flour, corn steep liquor, yeast extract, meat extract and urea, and inorganic nitrogen sources, such as ammonium salts of sulfuric acid, nitric acid, hydrochloric acid, carbonic acid and the like, gaseous ammonia and aqueous ammonia, each singly or in adequate combination. In addition, various inorganic salts necessary for the growth of the bacterial strain employed, for example salts of calcium, potassium, sodium, magnesium, manganese, iron, copper, zinc, etc. with sulfuric acid, hydrochloric acid, carbonic acid, phosphoric acid, acetic acid, etc., as well as amino acids, vitamins and other factors necessary for the growth of said bacterial strain may be added to the medium either singly or in appropriate combination. Furthermore, an antifoam, such as a silicone oil, may be used as necessary.

In this connection, the calcium and magnesium concentrations necessary for the growth of a polyglutamic acid-producing Bacillus strain, for instance, in the medium are about 0.7 millimole and about 2 millimoles, respectively, per liter.

The medium pH should preferably be adjusted as mentioned hereinabove. When the pH varies during cultivation, gaseous or aqueous ammonia, urea, an alkali hydroxide or the like may be added to the medium in an amount sufficient for adjusting the pH to a desired level. The cultivation temperature may be selected suitably with due consideration for the optimum growth temperature for the microorganism employed, among others. Generally, cultivation is carried out at a temperature of about 25° C. to about 40° C. for a period sufficient for the accumulation of polyglutamic acid to reach a maximum, normally for 20 to 72 hours.

The polyglutamic acid salts produced in the practice of the invention mainly comprise the salt with the alkaline earth metal ion used in the fermentation and in part the salts with other metals added as medium components. These polyglutamic acid salts may be isolated and purified by per se known means and may be converted to free polyglutamic acid or the sodium, potassium, ammonium or some other salt, as necessary, with consideration for the use thereof.

EXAMPLES

The following experimental examples and working examples are further illustrative of the present invention.

EXPERIMENTAL EXAMPLE 1

*Bacillus subtilis* S-2 (IFO 14898, FERM BP-2528) was inoculated into the medium specified below in Table 1 and cultured at 37° C. for 16 hours.

TABLE 1

| Component | g/l |
|---|---|
| Glucose | 40 |
| Urea | 3 |
| $(NH_4)_2SO_4$ | 1 |
| $MgSO_4.7H_2O$ | 2 |
| $CaCl_2$ | 2 |
| $FeSO_4.7H_2O$ | 0.02 |
| Corn steep liquor | 10 |

A 60-ml portion of this culture broth was transplanted into 2 liters of each sterilized (120° C., 20 minutes) medium, specified in Table 2 with respect to its composition, and cultivation was conducted at a rate of aeration of 1 liter per minute and a temperature of 37° C. for 24 hours with stirring at 800 revolutions per minute. During cultivation, the pH was adjusted to and maintained at 6.5 using aqueous ammonia.

TABLE 2

| | (g/l) | | |
|---|---|---|---|
| | Medium (1) | Medium (2) | Medium (3) |
| Glucose | 40 | 60 | 80 |
| $(NH_4)_2SO_4$ | 2 | 2 | 2 |
| $MgSO_4.7H_2O$ | 0.5 | 0.5 | 0.5 |
| NaCl | 0.5 | 0.5 | 0.5 |
| $CaCl_2$ | 0.1 | 0.1 | 0.1 |
| $MnSO_4$ | 0.002 | 0.002 | 0.002 |
| L-Glutamic acid | 15 | 22.5 | 30 |
| $CaCO_3$ | 5 | 7.5 | 10 |

(Note 1) Biotin (100 μg/liter) was added to each medium.
(Note 2) The L-glutamic acid and $CaCO_3$ were dissolved in advance in water in the above weight ratio for neutralization, and the solution was then separately sterilized and admixed with the other medium components.

In addition, the media (1), (2) and (3) specified in Table 2 were modified by using 4.3, 6.45 and 8.6 g/liter of $MgCO_3$, respectively, in lieu of the $CaCO_3$ and cultivation was carried out in the same manner as mentioned above.

The polyglutamic acid content in each culture broth obtained was determined by colorimetry using the supernatant obtained by centrifugation for bacterial cell removal following appropriate dilution of the culture broth. The colorimetric method used was that described by Mitsuo Torii in "Kodenhishokuho (Photoelectric colorimetry), Itemized Discussion 2", page 110 (edited by T. Sekine, T. Sasagawa, S. Morita, T. Kimura and K. Kuratomi, published by Nankodo, 1958). Assay results are shown in Table 3.

TABLE 3

| Alkaline earth metal salt | | Glutamic acid (g/liter) | Glucose (g/liter) | Polyglutamic acid (g/liter) |
|---|---|---|---|---|
| Name | Addition level (g/liter) | | | |
| $CaCO_3$ | 5 (0.05) | 15 | 40 | 14.2 |
| | 7.5 (0.075) | 22.5 | 60 | 18.6 |
| | 10 (0.10) | 30 | 80 | 21.5 |
| $MgCO_3$ | 4.3 (0.051) | 15 | 40 | 14.6 |
| | 6.45 (0.076) | 22.5 | 60 | 19.0 |
| | 8.6 (0.10) | 30 | 80 | 22.1 |

Each numerical figure in the parentheses indicates the corresponding molar concentration.

As shown in Table 3, the addition of $CaCO_3$ or $MgCO_3$ resulted in an increased production of polyglutamic acid with the increase in the level of addition of L-glutamic acid. Comparative runs were conducted by adding $NH_4OH$, NaOH and KOH each in lieu of $CaCO_3$ or $MgCO_3$ and proceeding in the same manner but failed to cause a significant increase in the yield of polyglutamic acid even when the level of addition of L-glutamic acid was doubled.

EXPERIMENTAL EXAMPLE 2

Media were prepared which contained, each in two liters, 60 g of glucose, 60 g of L-glutamic acid and 2 g, 5 g, 10 g, 20 g, 30 g or 40 g of $CaCO_3$ and otherwise had the same composition as the media given in Table 2. The L-glutamic acid and $CaCO_3$ were mixed together in advance and, after 20 minutes of sterilization at 121° C., the mixture was blended with the other medium components. Using these media and using *Bacillus subtilis* S-2 (IFO 14898, FERM BP-2528) as the seed, cultivation was carried out in the same manner as in Experimental Example 1 in a 5-liter jar fermenter and the amounts of polyglutamic acid accumulated were determined. The assay results thus obtained are shown in Table 4. These results clearly indicate that the accumulation of polyglutamic acid increased in proportion to the level of addition of $CaCO_3$ and, at the addition level of 10 g $CaCO_3$ per liter, about 22 g per liter of polyglutamic acid was obtained. When the same experimental procedure was followed using $MgCO_3$ in lieu of $CaCO_3$, the accumulation of polyglutamic acid increased with the level of addition of $MgCO_3$, as shown in Table 5; at the addition level of 10 g or more $MgCO_3$ per liter, the accumulation of polyglutamic acid amounted to 22 g per liter.

TABLE 4

| $CaCO_3$ (g/liter) | | Polyglutamic acid accumulated (g/liter) |
|---|---|---|
| 1 | (0.01) | 10.5 |
| 2.5 | (0.025) | 11.8 |
| 5 | (0.05) | 16.2 |
| 7.5 | (0.075) | 19.0 |
| 10 | (0.10) | 22.5 |
| 15 | (0.15) | 22.0 |
| 20 | (0.20) | 21.9 |

Each numerical figure in the parentheses indicates the corresponding molar concentration.

TABLE 5

| $MgCO_3$ (g/liter) | | Polyglutamic acid accumulated (g/liter) |
|---|---|---|
| 1.0 | (0.012) | 11.2 |
| 2.5 | (0.030) | 13.0 |
| 5.0 | (0.059) | 17.9 |
| 7.5 | (0.089) | 20.5 |
| 10 | (0.119) | 22.7 |
| 15 | (0.178) | 22.3 |
| 20 | (0.237) | 23.0 |

Each numerical figure in the parentheses indicates the corresponding molar concentration.

EXAMPLE 1

L-Glutamic acid (60 g) was suspended in 300 ml of pure water and neutralized by addition of 14.8 g of $Ca(OH)_2$ or 11.6 g of $Mg(OH)_2$. The mixture was then diluted to 500 ml and sterilized. Separately, a medium was prepared in an amount of 2 liters which contained 30 g/liter of glucose and otherwise had the same composition as the media specified in Table 2, and a 1.5-liter portion thereof was placed in a 5-liter jar fermenter and sterilized at 121½° C. for 20 minutes. The medium was inoculated with 60 ml of a seed culture of *Bacillus subtilis* S-2 (IFO 14898, FERM BP-2528) grown in the seed culture medium specified in Table 1, the neutralization product prepared from L-glutamic acid and $Ca(OH)_2$ or $Mg(OH)_2$ as mentioned above was added, and fermentation was conducted under the same conditions as used in Experimental Example 1 for 24 hours. Polyglutamic acid was accumulated in the culture broth apparently in an increased amount, as shown by the data given in Table 6.

TABLE 6

| | Concentration (g/liter) | Polyglutamic acid accumulated (g/liter) |
|---|---|---|
| $Ca(OH)_2$ | 7.4 (0.1 mole/liter) | 20.3 |
| $Mg(OH)_2$ | 5.8 (0.1 mole/liter) | 19.8 |

EXAMPLE 2

L-Glutamic acid (30 g) was suspended in each of two 150-ml portions of pure water, 10 g of $CaCO_3$ was added to each suspension, and each mixture as diluted to 250 ml. Separately, 2 liters of a medium (main medium) was prepared which contained 30 g/liter of glucose and otherwise had the same composition as the media specified in Table 2, and a 1.5-liter portion thereof was taken and charged into a 5-liter jar fermenter and sterilized at 121° C. for 20 minutes. This medium was inoculated with 60 ml of a seed culture of *Bacillus subtilis* S-2 (IFO 14898, FERM BP-2528) as prepared in the same manner as in Experimental Example 1, one 250-ml portion of the calcium L-glutamate-containing liquid mentioned above was added, and cultivation was started. After 6 hours of cultivation, the remaining 250-ml portion of the calcium L-glutamate preparation was fed portionwise over 6 hours. After 24 hours of cultivation, about 1.95 liters of a culture broth containing polyglutamic acid accumulated in a concentration of 24.5 g/liter was obtained. Ethanol (1.0 liter) was added gradually to the broth, whereupon a fibrous precipitate formed. The precipitate was collected by filtration through gauze and dried under reduced pressure. Thus was obtained 45.3 g of calcium polyglutamate.

What we claim is:

1. A method for producing polyglutamic acid or a salt thereof which comprises cultivating a microorganism in a medium continaing an alkaline earth metal ion at a concentration of not less than 0.05 mole per liter, wherein said microorganism is selected from the group consisting of the *Bacillus subtilis* strain having deposit number FERM BP-2528 and *Bacillus licheniformis* IFO 12107 and wherein said microorganism produces a polyglutamic acid.

2. A method according to claim 1, wherein the alkaline earth metal ion is calcium ion, magnesium ion or barium ion.

3. A method according to claim 1, wherein the concentration is within the range of 0.05 to 0.3 mole per liter.

* * * * *